United States Patent [19]
Hofmann

[11] Patent Number: 5,970,119
[45] Date of Patent: Oct. 19, 1999

[54] RADIOLOGICAL SCALING AND ALIGNMENT DEVICE

[75] Inventor: Lawrence Vincent Hofmann, Baltimore, Md.

[73] Assignee: Douglas Holtz (part interest), London, United Kingdom

[21] Appl. No.: 08/972,593

[22] Filed: Nov. 18, 1997

[51] Int. Cl.$^6$ ............................. H05G 1/28; G01D 18/00
[52] U.S. Cl. ............................................. 378/163; 378/207
[58] Field of Search .................................. 378/162, 163, 378/205, 207

[56] References Cited

U.S. PATENT DOCUMENTS

| | | | |
|---|---|---|---|
| 1,396,920 | 11/1921 | Brostrom | 378/163 |
| 3,706,883 | 12/1972 | McIntyre | 378/163 |
| 4,061,924 | 12/1977 | Jacoby et al. | 378/162 |
| 4,850,866 | 7/1989 | Gutierrez et al. | 433/72 |
| 4,878,842 | 11/1989 | Malcmacher et al. | 433/72 |
| 5,008,947 | 4/1991 | Yamada | 378/162 |
| 5,216,700 | 6/1993 | Cherian | 378/163 |
| 5,224,147 | 6/1993 | Collin et al. | 378/163 |
| 5,463,669 | 10/1995 | Kaplan | 378/205 |

*Primary Examiner*—David P. Porta
*Assistant Examiner*—Drew A. Dunn
*Attorney, Agent, or Firm*—Frishauf, Holtz, Goodman, Langer & Chick, P.C.

[57] ABSTRACT

A radiological scaling device for use in determining a size of an anatomic structure on an X-ray image comprises a radio-opaque member having a predetermined known length, and first and second radio-lucent visualization gaps provided in the radio-opaque member. The radio-opaque member may be incorporated in a handle device or a catheter device such that the radio-opaque member may manipulated to be aligned in substantially a same plane as the anatomic structure between an X-ray tube and a film, and substantially perpendicular to an X-ray beam emitted by the X-ray tube. An X-ray image is produced which includes first and second gaps corresponding to the first and second radio-lucent visualization gaps of the radio-opaque member to thereby confirm that the radio-opaque member has been properly aligned substantially perpendicular to the X-ray beam. An apparent length of the radio-opaque member and an apparent length of the anatomic structure on the resultant X-ray image are measured, and the size of the anatomic structure is then calculated based on the known length of the radio-opaque member, the measured apparent length of the radio-opaque member, and the measured apparent length of the anatomic structure.

17 Claims, 10 Drawing Sheets

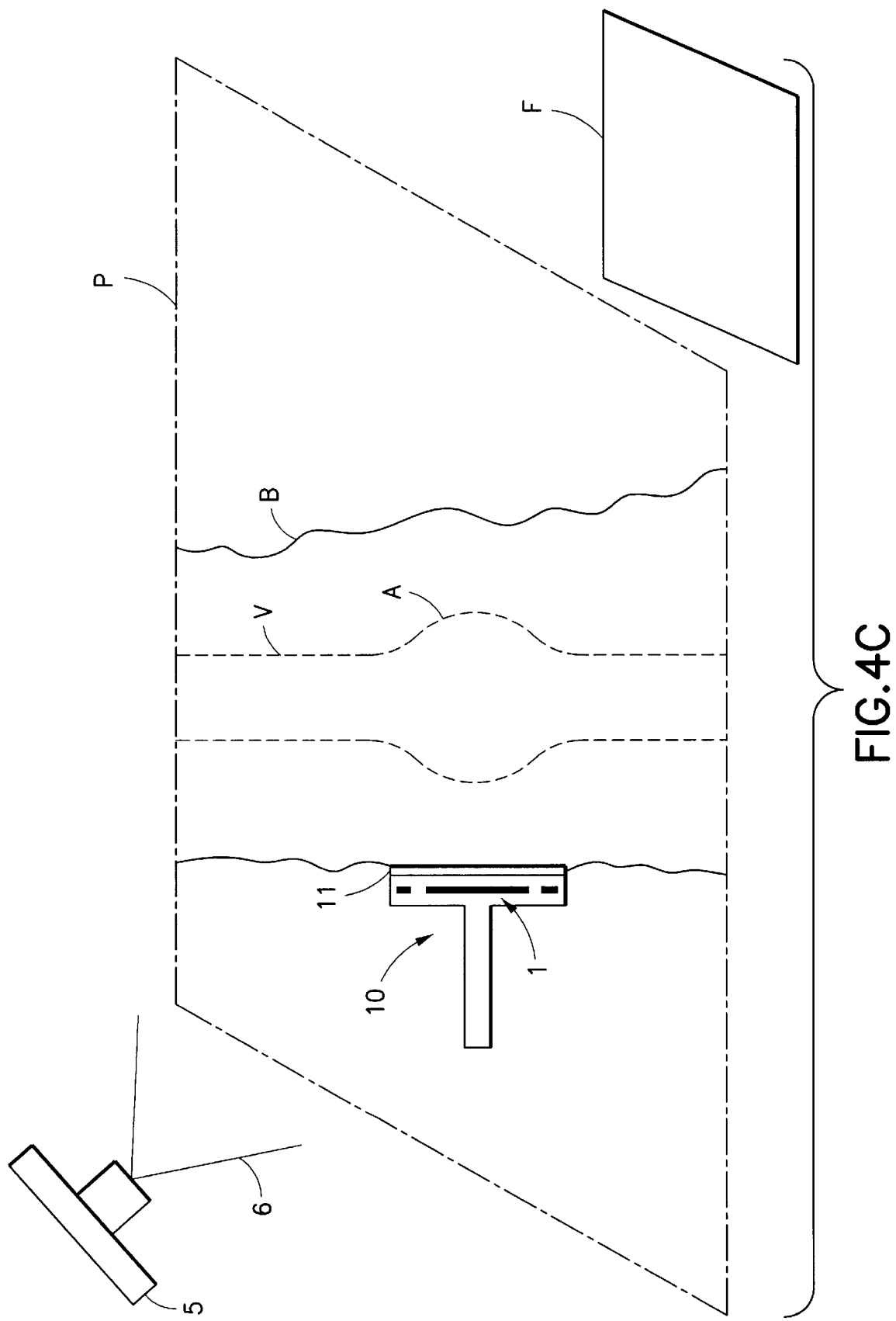

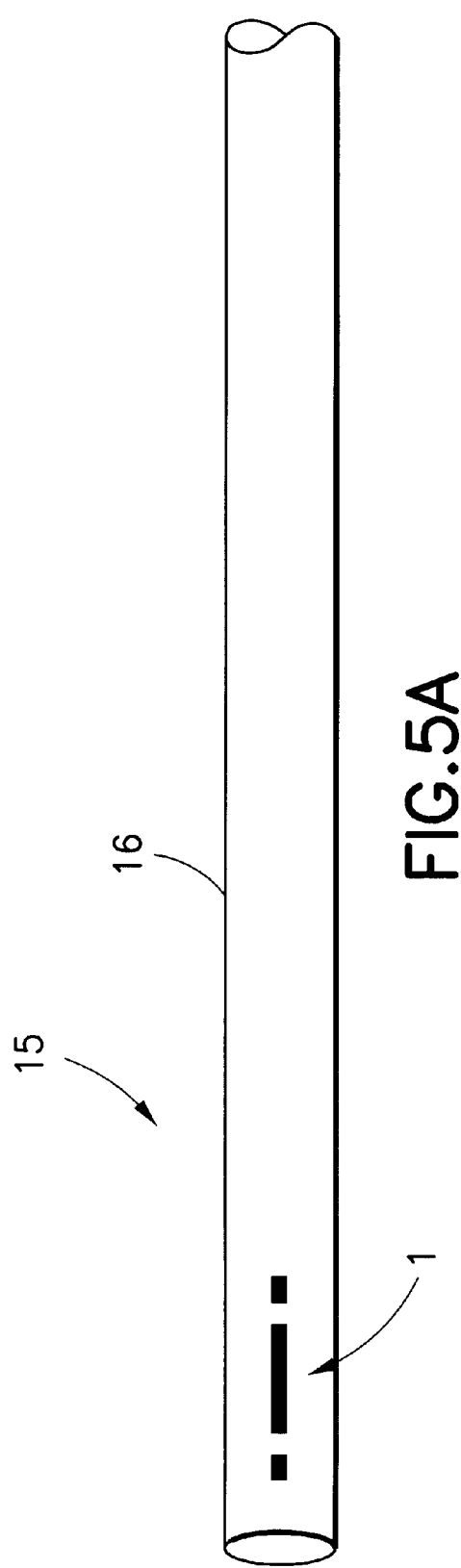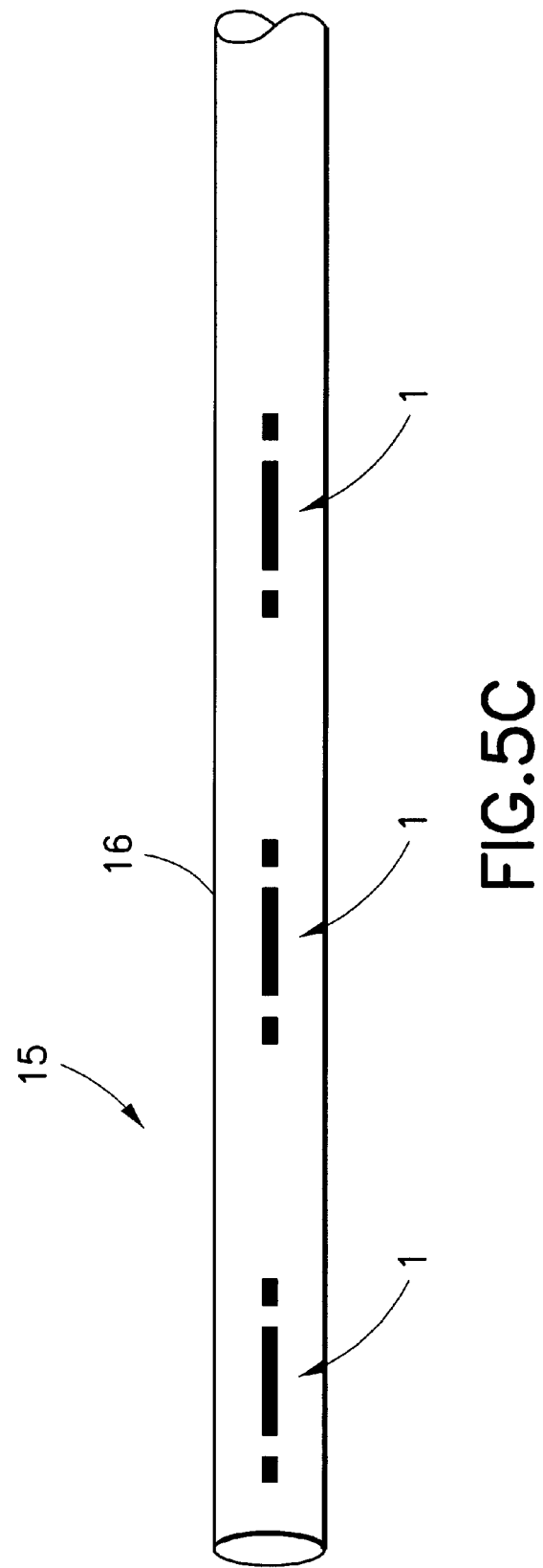

RADIOLOGICAL SCALING AND ALIGNMENT DEVICE

BACKGROUND OF THE INVENTION

The present invention relates to a radiological scaling device which enables the actual anatomical size of a given structure on a radiological image such as an X-ray image to be accurately calculated.

Currently, it is difficult to determine the actual anatomic size of a given structure on an X-ray image. The determination of the actual anatomic size of a given structure is particularly important in fluoroscopy, wherein a procedure is carried out by a physician in coordination with continuous X-ray imaging of the patient.

In fluoroscopy, an image will often be magnified on a screen to aid a physician in seeing small catheters or structures. Measuring the apparent size of an object on a magnified X-ray image will often yield a falsely enlarged value. In particular, when an object-to-film distance is varied so as to accommodate for different sized patients, the size of an object on an X-ray image is increased or decreased, much like the size of a hand shadow on a movie screen is increased or decreased by varying the distance of the hand from the screen.

Many interventional radiology procedures require accurate determination of the size of different anatomic structures. For example, angioplasty and/or stent placement in blood vessels, bile ducts or bronchi require appropriate size determinations of these structures. These structures as well as different types of pathology such as aneurysms, tumors, and strictures are currently difficult to quantitatively measure.

Presently, physicians typically rely on past experience to judge the size of an anatomic structure, which often leads to inaccurate determinations. Alternatively, a "marker" catheter having two small radio-opaque markers spaced approximately two centimeters apart may be used to determine the size of an anatomic structure by a direct arithmetic proportional calculation based upon observed apparent lengths. However, there are several problems with the conventional marker catheter. First, it is often difficult to include both the markers and the anatomic region of interest on the same X-ray image during a procedure. Second, because the conventional marker catheter does not have any mechanism for ensuring that a line extending between the two markers is aligned perpendicular to the X-ray beam, angulation of the X-ray beam can foreshorten the apparent distance between the two markers on the X-ray image, resulting in an inaccurate determination of the size of the anatomic structure in question. Third, the conventional marker catheter is designed for intravascular use, and ignores biliary and bronchial applications. And lastly, a physician may begin a procedure with an unmarked catheter and may not realize until the procedure is already under way that it is desirable to measure a size of a structure, in which case it becomes difficult, time-consuming and expensive to exchange an unmarked catheter for a marker catheter.

U.S. Pat. No. 5,216,700 discloses a tape having a graduated scale with a flexible rib for providing location indicia during an X-ray process. This patent, however, does not disclose using such a tape for sizing structures, and inaccurate results would be generated if this tape were used for sizing structures. That is, because the tape disclosed in U.S. Pat. No. 5,216,700 conforms to the curves of the body and because no mechanism is provided for ensuring that the tape is always perpendicular to the X-ray beam, the apparent length of the device on the X-ray image could be foreshortened.

U.S. Pat. No. 4,850,866 discloses a method and apparatus for measuring the length of the root canal of a tooth by placing a probe of known length into the canal and making an X-ray exposure thereof. However, this technique also does not ensure that the probe is positioned perpendicular to the X-ray beam, so that inaccurate results may again be generated.

SUMMARY OF THE INVENTION

It is an object of the present invention to provide a reliable and accurate device for determining the size of an anatomic structure on an X-ray image.

In order to achieve this object, the radiological scaling device of the present invention comprises a radio-opaque member of a predetermined known length and at least one radio-lucent visualization gap provided in the radio-opaque member.

More specifically, the scaling device of the present invention may, for example, comprise a radio-opaque member having first and second radio-lucent visualization gaps provided symmetrically at respective end portions of the radio-opaque member. The radio-opaque member may be provided in a housing having a handle portion for manipulating the scaling device so as to attach the scaling device to an external surface of a patient. Alternatively, the radio-opaque member may be provided in a catheter for insertion into a blood vessel or body part of the patient.

In use, the scaling device is arranged in a vicinity of the anatomic structure in question such that the radio-opaque member is aligned in substantially a same plane as the anatomic structure between an X-ray tube and a film, and substantially perpendicular to an X-ray beam emitted by the X-ray tube. An X-ray image is produced which includes at least one gap corresponding to the at least one radio-lucent visualization gap of the radio-opaque member to thereby confirm that the radio-opaque member has been properly aligned substantially perpendicular to the X-ray beam. An apparent length of the radio-opaque member and an apparent length of the anatomic structure on the X-ray image are measured, and the size of the anatomic structure is then calculated based on the known length of the radio-opaque member and the measured apparent lengths of the radio-opaque member and the anatomic structure.

BRIEF DESCRIPTION OF THE DRAWINGS

FIG. 4C is a view of the handle embodiment shown in FIGS. 4A and 4B attached to an external surface of a patient undergoing an angiogram for use in measuring a size of the blood vessel and an aneurysm in the patient.

FIG. 5A is a perspective view of an embodiment of the scaling device of the present invention wherein the radio-opaque member is provided in a catheter.

FIG. 5C is a perspective view of a catheter embodiment including a plurality of radio-opaque members.

DETAILED DESCRIPTION

Figure 1:
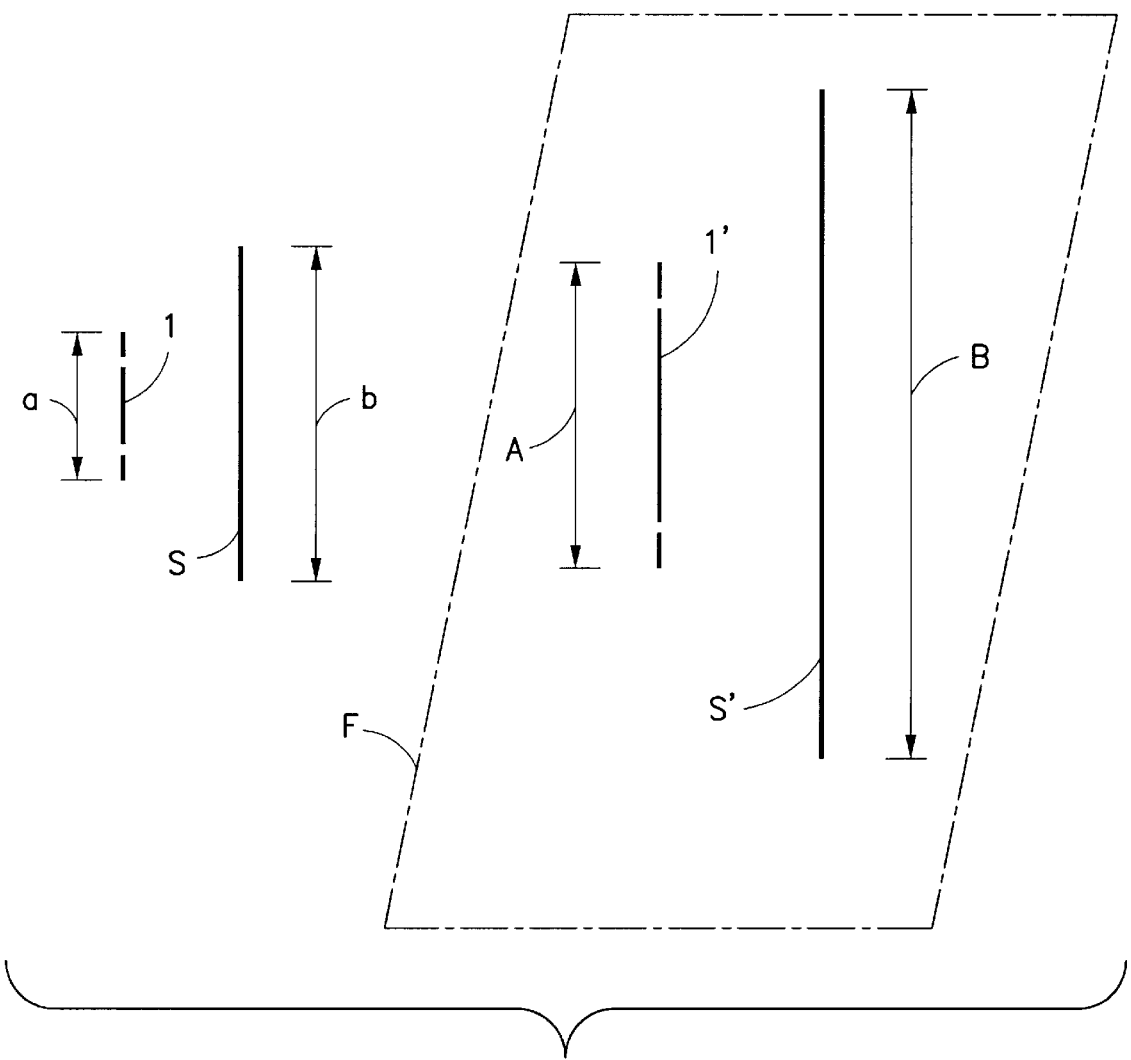
FIG. 1 is a schematic representation of the underlying operational principle of the scaler of the present invention.

FIG. 1 shows a schematic representation of the underlying operational principle of the scaling device of the present invention including a radio-opaque member 1. As shown in FIG. 1, the actual known length of the radio-opaque member 1 is represented as "a", and the actual length of an anatomic structure S whose size is to be measured is represented as "b". Also as shown in FIG. 1, the apparent length of the image 1' of the radio-opaque member 1 on an X-ray image formed on a film F is represented as "A", and the apparent length of the image S' of the anatomic structure S on the X-ray image formed on the film F is represented as "B". The apparent lengths "A" and "B" can be measured using any conventional technique, including, for example, use of a ruler, mechanical calipers or computer calipers. Thus, since the actual length "a" of the radio-opaque member 1 is known, the actual length "b" of the anatomic structure S can be calculated according to the following equations:

$$a/A = b/B \rightarrow b = B \times a/A$$

Figure 2:
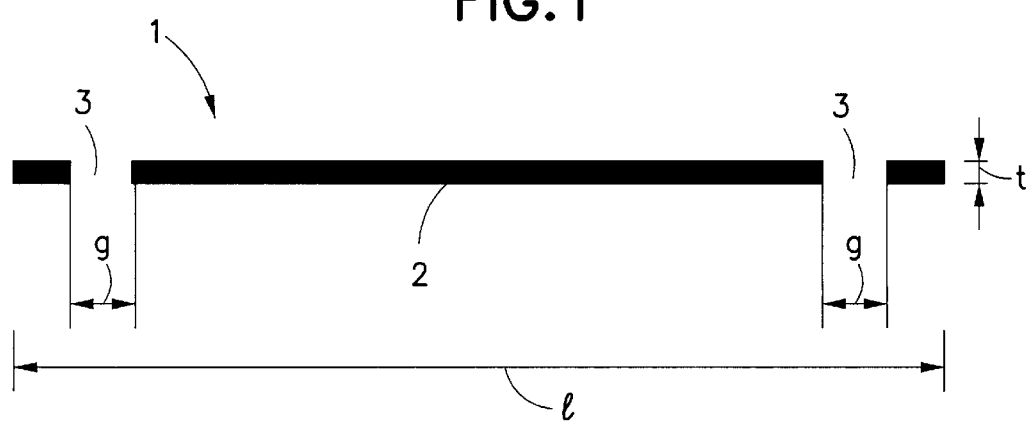
FIG. 2 is a schematic representation of a basic embodiment of the radio-opaque member of the present invention including two radio-lucent visualization gaps.

FIG. 2 shows a schematic representation of a basic embodiment of the radio-opaque member 1 of the present invention. The radio-opaque member 1 comprises a radio-opaque wire 2 which is provided with first and second radio-lucent visualization gaps 3 at respective end portions thereof. The wire 2 may be made out of any suitable radio-opaque metal or plastic material, and the visualization gaps 3 may each comprise a complete break in the radio-opaque wire 2, so that the wire 2 is broken into three separate portions.

The length l of the radio-opaque member 1 is set to be small enough to fit on the skin of small body parts such as a patient's neck or arm, and large enough to be clearly seen on an X-ray image. For example, the length l of the radio-opaque member 1 may be set at approximately 2.0 cm.

The thickness t of the radio-opaque member 1 must also be large enough to be clearly seen on an X-ray image. For example, the thickness t of the radio-opaque member 1 may be set at approximately 2 mm. As shown in FIG. 2, the radio-lucent visualization gaps 3 are equal in size and are positioned symmetrically at respective end portions of the radio-opaque member 1 so as to ensure the highest sensitivity to X-ray beam angulation. The gap size g of the radio-lucent visualization gaps 3 is also set to be large enough to be clearly seen on an X-ray image. For example, the gap size g of the radio-lucent visualization gaps 3 may each be set at approximately 0.3–0.5 mm in length.

The above-mentioned specific dimensions are not fixed, and the scaling device of the present invention will accurately operate within a wide range of dimensions. As described hereinbelow, the radio-opaque member 1 is utilized to ensure proper perpendicular alignment of the scaling device of the present invention with respect to an X-ray beam so as to avoid foreshortening of the respective apparent lengths of the radio-opaque member 1 and an anatomic structure of interest on a resultant X-ray image. Accordingly, a critical feature of the present invention is that the visualization gaps 3 are sized so as to enable corresponding gaps to be seen on the resultant X-ray image only when the radio-opaque member 3 is substantially perpendicular to the X-ray beam. That is, the visualization gaps 3 must be large enough so as to generate corresponding gaps which can be clearly seen on an X-ray image, but the visualization gaps 3 must not be so large that corresponding gaps will be seen on the X-ray image when the radio-opaque member 1 is not substantially perpendicular to the X-ray beam. In other words, the visualization gaps 3 are sized to generate corresponding gaps on the X-ray image over only a limited range of non-perpendicularity with respect to the X-ray beam.

The known length of the radio-opaque member 1 which is utilized to calculate the actual length of an anatomic structure in question does not necessarily have to be the total length 1 of the radio-opaque member 1 shown in FIG. 2. Alternatively, for example, a known length of the radio-opaque member between the visualization gaps 3 may also be utilized, and/or markers separated by a known distance may be provided on or in the vicinity of the radio-opaque member 1. Since, as explained hereinabove with respect to FIG. 1, the actual length of the anatomic structure in question is determined by a simple proportional relationship between a known length and two measured apparent lengths, any known length associated with the radio-opaque member 1 will suffice to calculate the actual length of the anatomic structure in question.

In order to ensure that the actual length of the anatomic structure in question is accurately determined, it is critical that the apparent lengths not be foreshortened on an X-ray image. It is with this aim in mind that the present invention has been conceived and reduced to practice.

Figure 3A:
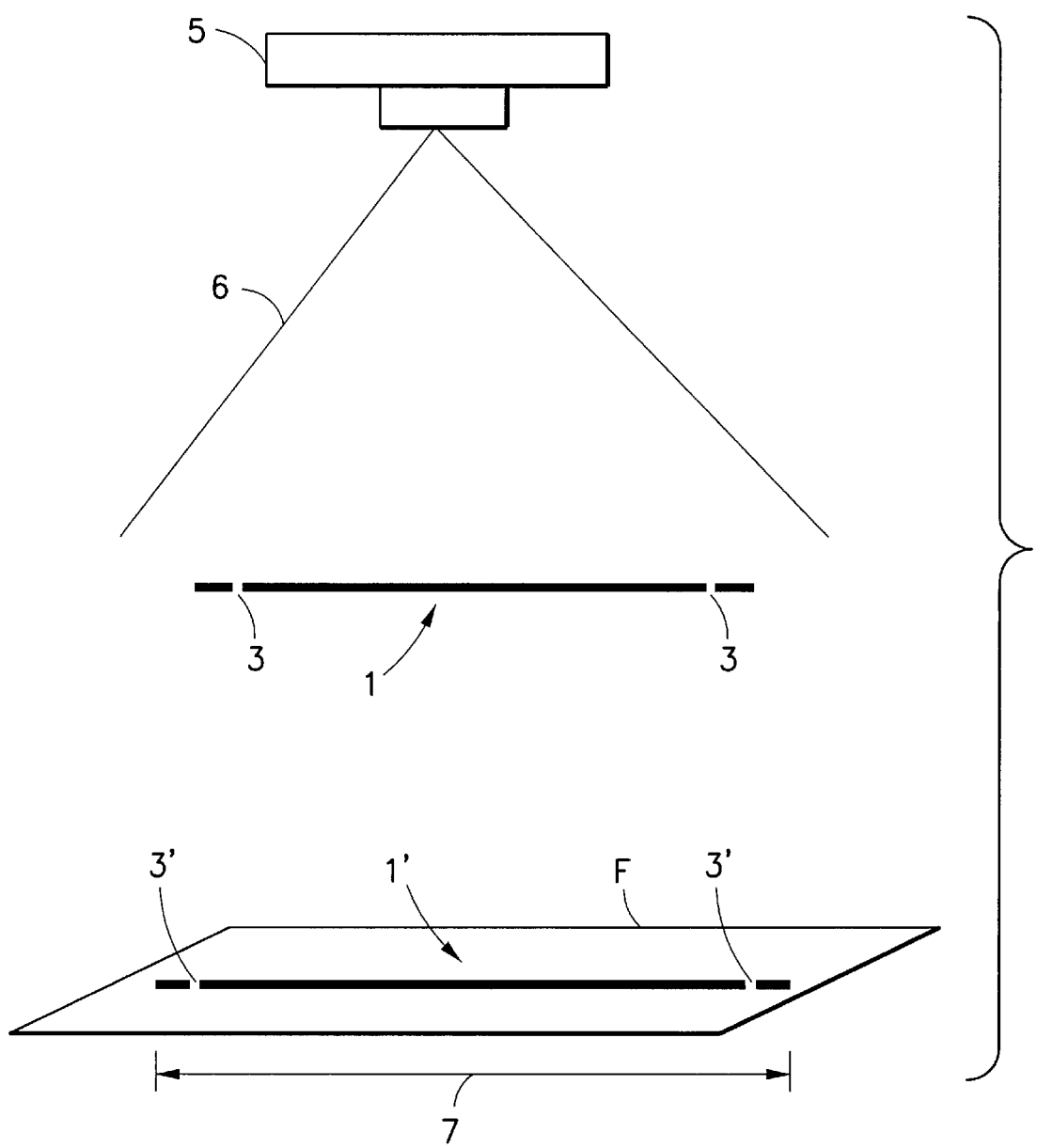
FIG. 3A is schematic representation of the radio-opaque member of the present invention in proper alignment substantially perpendicular to an X-ray tube and X-ray beam such that gaps corresponding to the visualization gaps can be seen on a resultant X-ray image.
Figure 3B:
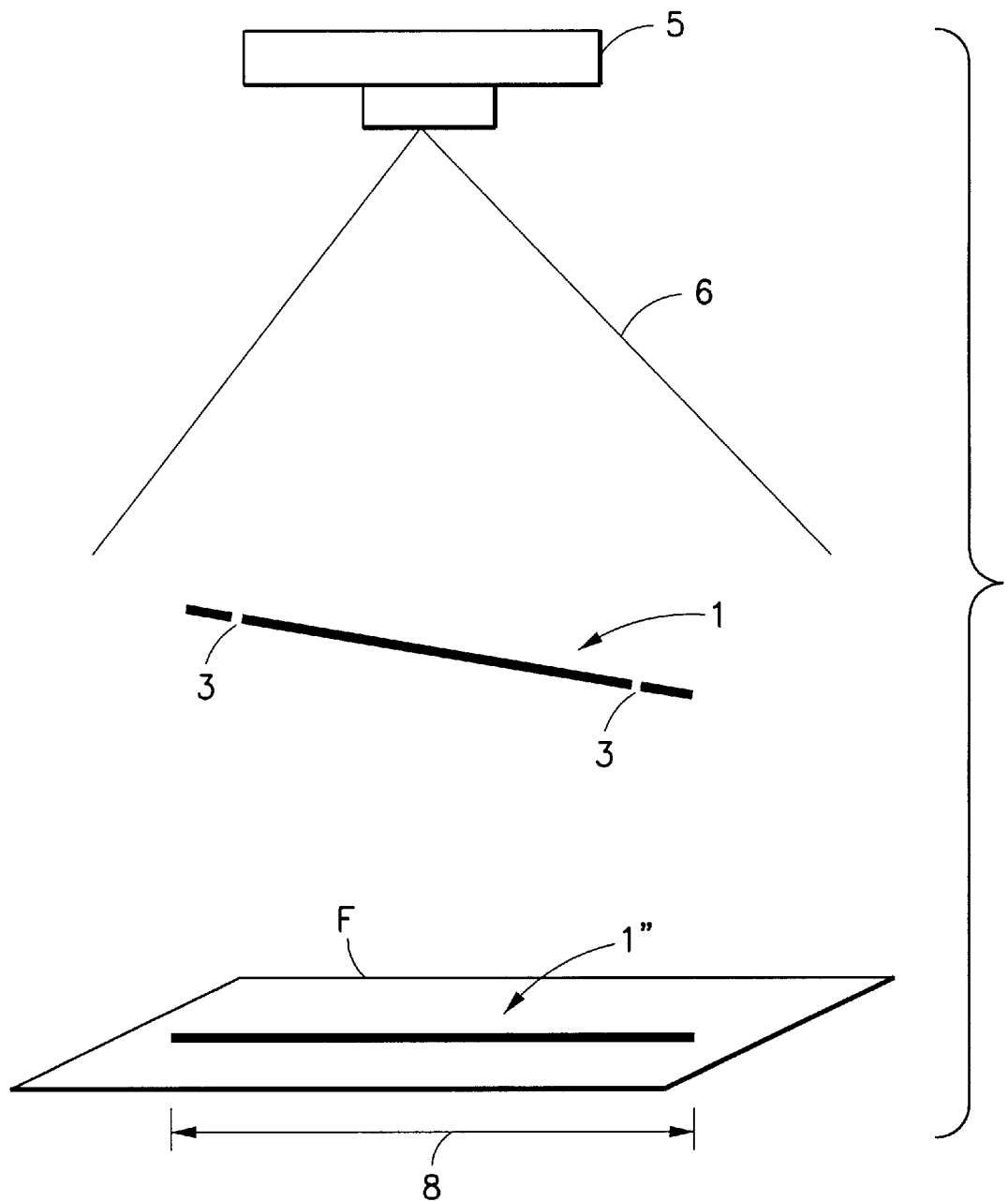
FIG. 3B is schematic representation of the radio-opaque member of the present invention not in proper perpendicular alignment with the X-ray tube and X-ray beam such that the resultant X-ray image does not include gaps corresponding to the visualization gaps and such that the apparent distances on the resultant X-ray image are foreshortened.

FIGS. 3A and 3B are schematic representations illustrating how the visualization gaps 3 of the present invention can be utilized to ensure proper perpendicular alignment of the radio-opaque member 1 with respect to an X-ray beam 6 emitted from an X-ray tube 5.

As shown in FIG. 3A, if the radio-opaque member 1 is properly aligned substantially perpendicular to the X-ray beam 6, the image 1' of the radio-opaque member 1 on a film F includes gaps 3' corresponding to the visualization gaps 3, and the apparent total length of the image 1' of the radio-opaque member 1 is indicated by the reference numeral 7. The size of the anatomic structure can then be accurately calculated based on this apparent length 7, the known length l of the radio-opaque member 1 and the apparent length of the anatomic structure.

As shown in FIG. 3B, however, if the radio-opaque member 1 is not properly aligned perpendicular to the X-ray beam 6, the image 1" of the radio-opaque member 1 on the film F does not include gaps corresponding to the visualization gaps 3, and the apparent total length 8 of the radio opaque member 1 is foreshortened. If the size of the anatomic structure were calculated based on this foreshortened apparent length 8, an error would result.

Thus, in use, if the image of the radio-opaque member 1 on a resultant X-ray image does not include gaps corresponding to the. visualization gaps 3, then the physician is alerted that the radio-opaque member 1 is not properly aligned perpendicular to the X-ray beam emitted from the X-ray tube. In such case, the radio-opaque member 1 should be manipulated until the image of the radio-opaque member 1 on the resultant X-ray image includes gaps corresponding to the visualization gaps 3 so that the size of an anatomic structure in question can be accurately determined.

Figure 4A:
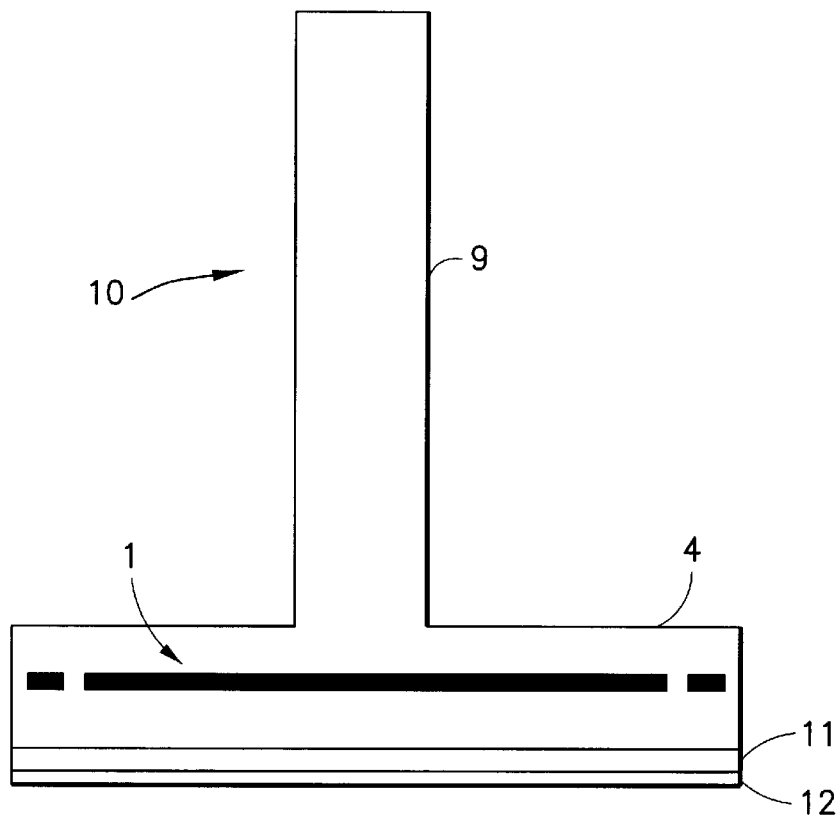
FIG. 4A is a front view of an embodiment of the scaling device of the present invention wherein the radio-opaque member is provided in a housing having a handle portion.
Figure 4B:
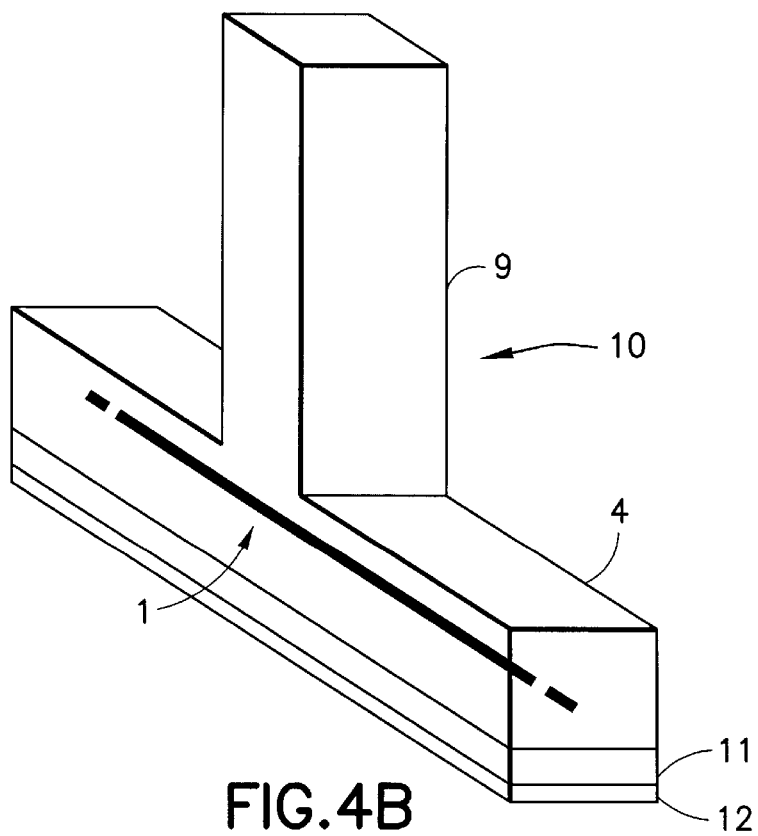
FIG. 4B is a perspective side view of the handle embodiment shown in FIG. 4A.

FIGS. 4A and 4B respectively show a front view and perspective side view of a handle device 10 wherein the radio-opaque member 1 is provided in a housing 4 having a handle portion 9. The housing 4 and handle portion 9 are arranged to have a T-shaped configuration, and may be formed from a solid block of molded radio-lucent material such as polycarbonate. As shown in FIGS. 4A and 4B, the radio-opaque member 1 is embedded in the housing 4. Alternatively, the radio-opaque member 1 may be superposed on the housing 4.

The handle portion 9 should be of a length sufficient so as to be easily grasped by the user's fingers, and may, for example, be approximately 2–3 cm long. However, since as shown in FIG. 4C the handle device 10 is typically positioned to extend outwardly away from an external surface of a patient, a gravitational force acts on the handle portion to pull the handle portion downward. Accordingly, the handle portion 9 should not be so long that an untoward torque is generated which might cause the handle device 10 to fall off the patient or interfere with the primary procedure being carried out by a physician.

A layer of adhesive 11 is provided on an external surface of the housing 4, and a peel-off cover strip 12 is provided on the adhesive 11. The adhesive 11 may be made out of any suitable essentially radio-lucent material that removably adheres to human skin, surgical drape and cloth, and the cover strip 12 may be made out of wax paper or any other similar suitable material that may be easily released and removed from the adhesive 11 prior to use of the handle device 10.

FIG. 4C is a view of the handle device 10 attached to an external surface of a patient undergoing an angiogram for use in measuring a size of a blood vessel V and aneurysm A in the patient. The cover strip 12 is removed, and the adhesive 11 is holding the handle device 10 to an external surface of body part B of the patient. The handle portion 9 is used to place the handle device 10 on the patient at a position adjacent to the blood vessel V having aneurysm A, such that the radio-opaque member 1 is in substantially a same plane P as the blood vessel V and aneurysm A above the film F and below the X-ray tube 5. Of course, the radio-opaque member 1 and the blood vessel V and aneurysm A should also be aligned substantially perpendicular to the X-ray beam 6.

FIG. 5A is a perspective view of a catheter device 15 wherein the radio-opaque member 1 is provided in a catheter 16. As used herein, the term catheter includes any flexible tube or guidewire insertable into the body. The catheter 16 may be made of any suitable essentially radiolucent material which enables the radio-opaque member 1 to be visualized on an X-ray image. For example, the catheter may be made of polyethylene. The radio-opaque member 1 may be longitudinally arranged along the length of the catheter 16 at an end portion thereof as shown in FIG. 5A, or the radio-opaque member 1 may be provided at any other suitable position along the length of the catheter 16.

More specifically, the radio-opaque member 1 may be embedded in the wall of the catheter 16, or may be superposed on either an inside or outside portion of the wall of the catheter. In addition, as shown in FIG. 5C, a plurality of radio-opaque members 1 may be incorporated in a single catheter 16 if, for example, the exact position of the structure whose size is to be measured is unknown or if, for example, the sizes of a plurality of internal structures are to be measured.

Figure 5B:
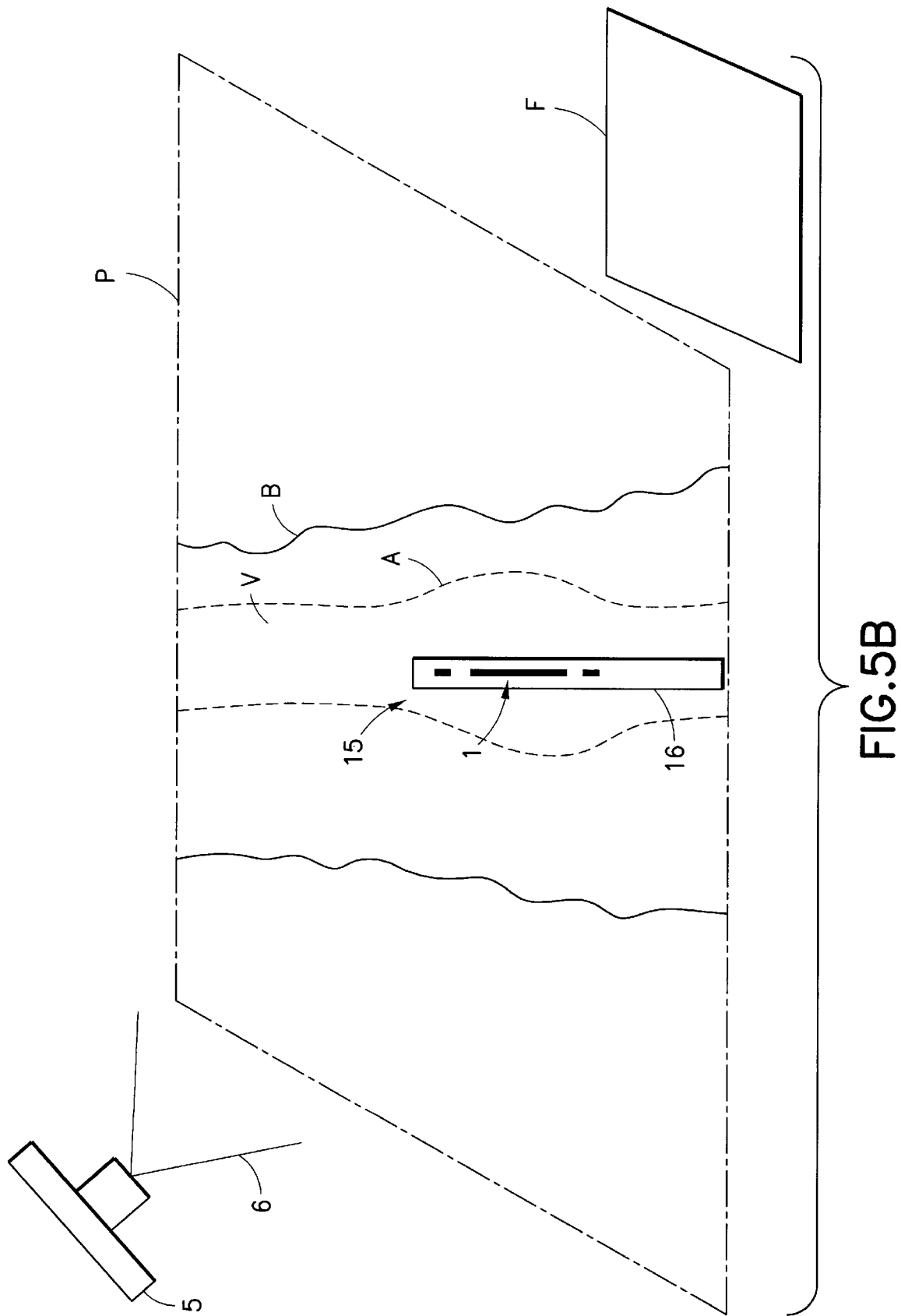
FIG. 5B is a view of the catheter embodiment shown in FIG. 5A inserted into a blood vessel of a patient undergoing an angiogram for use in measuring a size of the blood vessel and an aneurysm in the patient.

FIG. 5B is a view of the catheter device 15 inserted into a blood vessel V of a patient undergoing an angiogram for use in measuring a size of the blood vessel V and an aneurysm A in the patient. The catheter 16 is shown inserted in the blood vessel V of a body part B of the patient such that the radio-opaque member 1 is within the vicinity of the blood vessel V and aneurysm A, and such that the radio-opaque member 1 and blood vessel V and aneurysm A are in substantially a same plane P above the film F and below the X-ray tube 5. Of course, the radio-opaque member 1 and the blood vessel V and aneurysm A are again also aligned substantially perpendicular to the X-ray beam 6.

Figure 6:
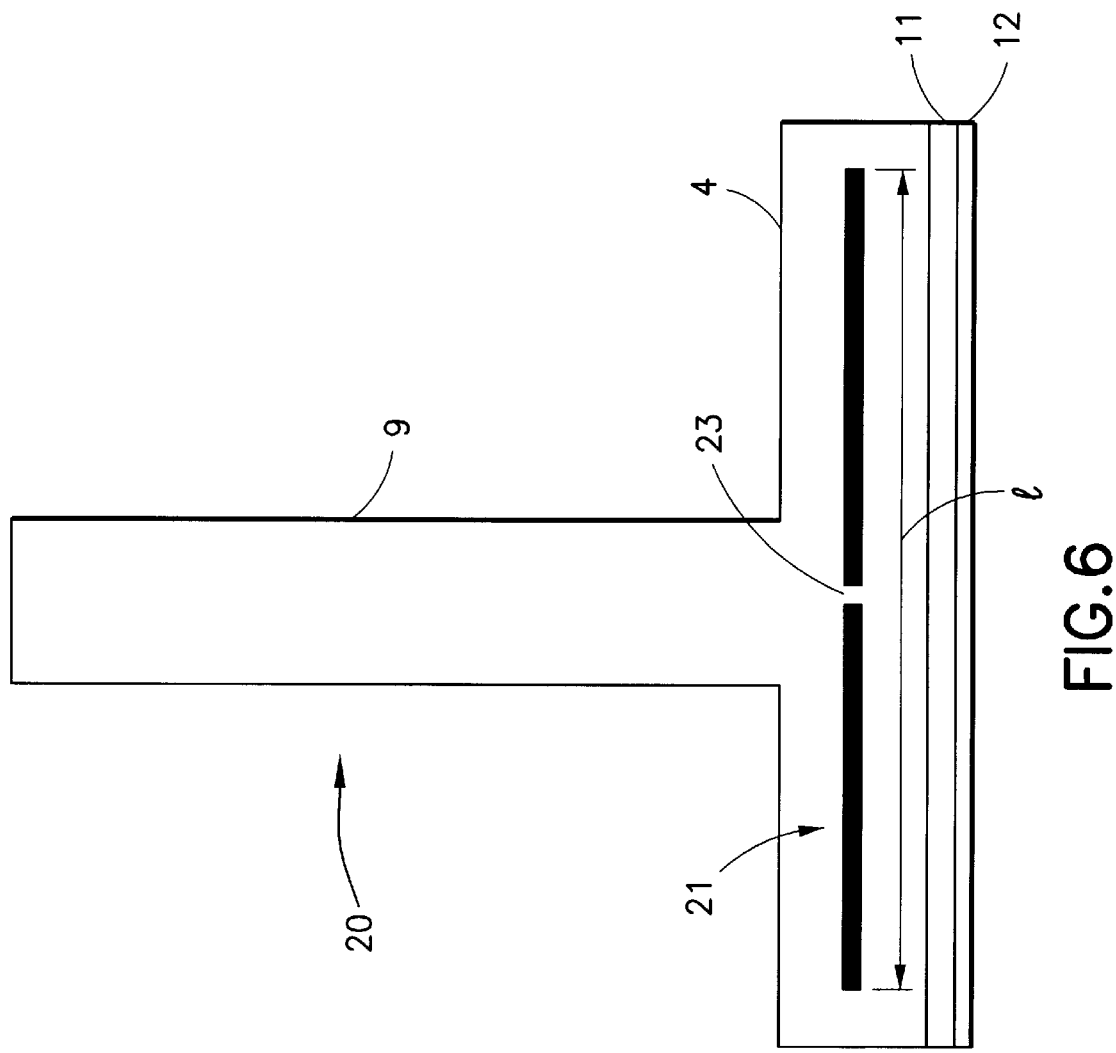
FIG. 6 is a schematic representation of an embodiment of the radio-opaque member of the present invention including only one visualization gap.

FIG. 6 is a front view of an alternative handle device 20 wherein a radio-opaque member 21 of the predetermined known length l includes only one visualization gap 23 in a center portion thereof. The handle device 20 is employed in a manner identical to the handle device 10 described hereinabove, whereby the visualization gap 23 generates only a single corresponding gap in a resultant X-ray image when the handle device 20 is properly aligned substantially perpendicular to the X-ray beam. When a gap is observed on the X-ray image, the apparent length of the radio-opaque member 21 and an apparent length of the anatomic structure on the resultant X-ray image are measured, and the size of the anatomic structure in question is then calculated based on the known length l of the radio-opaque member 21, the measured apparent length of the radio-opaque member 21, and the measured apparent length of the anatomic structure. The radio-opaque member 21 may be similarly employed in a catheter device in the manner described hereinabove with respect to the radio-opaque members 1 shown in FIGS. 5A–5C.

Figure 7:
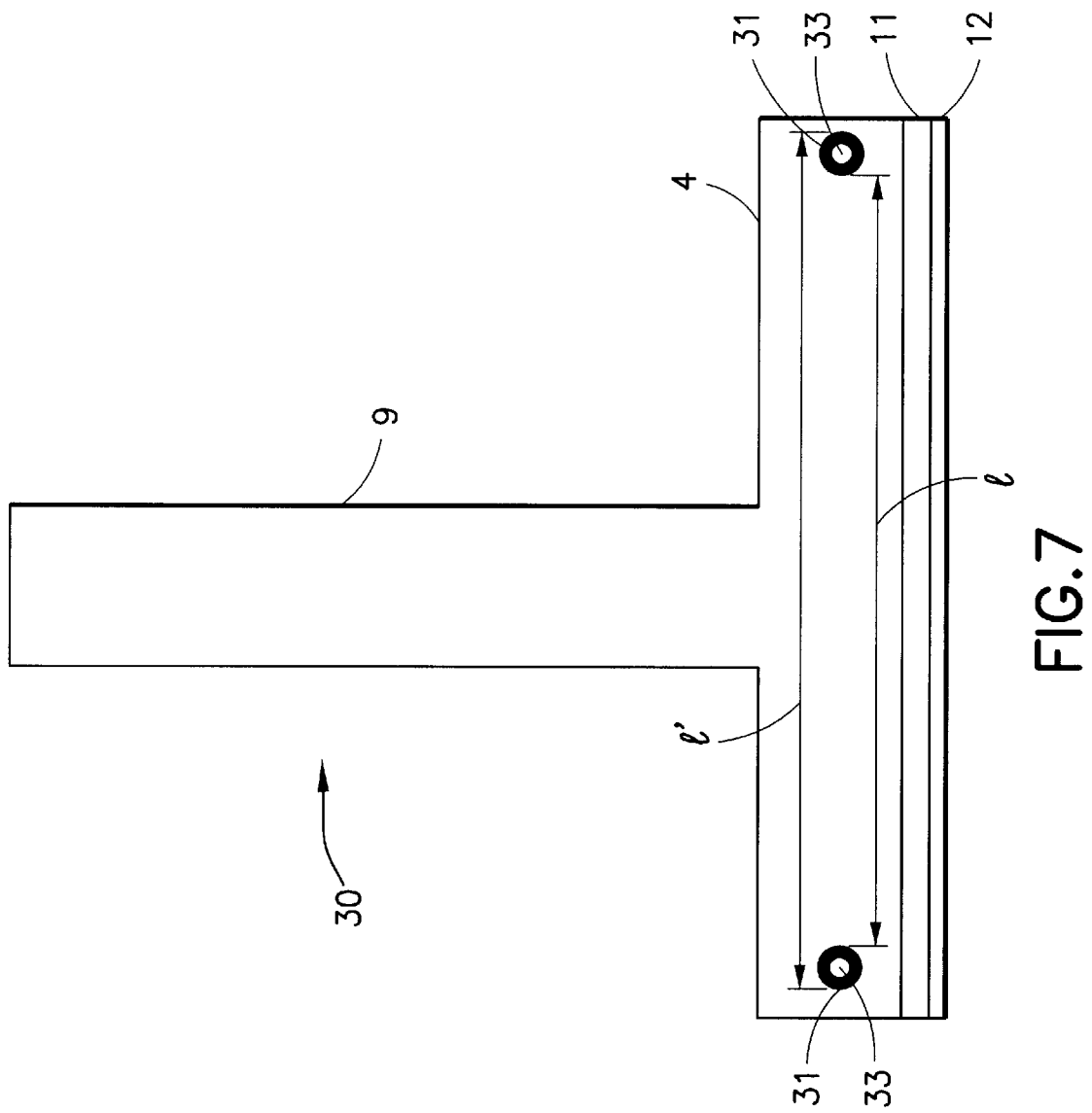
FIG. 7 is a perspective front view of an alternative embodiment of the scaling device wherein two washer shaped radio-opaque members are separated by a predetermined known length.

FIG. 7 is a front view of an alternative handle device 30 wherein two washer shaped, apertured radio-opaque members 31 are provided in a housing 32 separated by a predetermined known length. As shown in FIG. 7, the predetermined known length may be the distance l between the innermost portions of the radio-opaque members 31, or the distance l' between the outermost portions of the radio-opaque members 31. Each of the radio-opaque members 31 is provided with a radio-lucent visualization gap 33 in a center portion thereof. The handle device 30 is employed in a manner identical to the handle device 10 described hereinabove, whereby the visualization gaps 33 generate corresponding gaps in a resultant X-ray image when the handle device 30 is properly aligned substantially perpendicular to an X-ray beam. When gaps are observed on the X-ray image, an apparent length between the radio-opaque members 31 and an apparent length of the anatomic structure on the resultant X-ray image are measured, and the size of the anatomic structure is then calculated based on the predetermined known length between the radio-opaque members 31, the measured apparent length between the radio-opaque members 31, and the measured apparent length of the anatomic structure. Again, the radio-opaque members 31 may be similarly employed in a catheter device in the manner described hereinabove with respect to the radio-opaque members 1 shown in FIGS. 5A–5C.

Figure 8A:
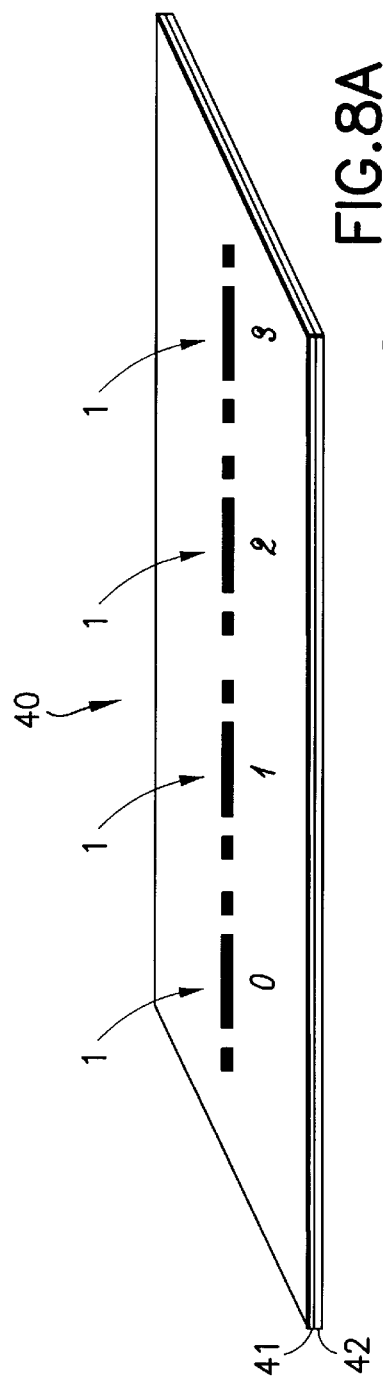
FIG. 8A is a perspective front view of another embodiment of the present invention wherein a plurality of radio-opaque members are provided in an adhesive tape which can be applied to the outside of a patient's body.

FIG. 8A is a perspective front view of another embodiment of the present invention wherein a plurality of radio-opaque members 1 are longitudinally arranged in an adhesive tape 40 which can be applied to the outside of a patient's body. The adhesive tape comprises an adhesive layer 41 which can be removably attached to the skin of a patient, preferably without causing pain, and a peel-off cover layer 42 which can be easily released and removed from the adhesive layer 41 prior to use. Alternatively, the adhesive tape may comprise an adhesive layer which is wrapped around itself to form a roll. The adhesive tape is preferably essentially radio-lucent.

As shown in FIG. 8A, each of the respective radio-opaque members 1 has a corresponding indicia associated therewith. The indicia shown in FIG. 8A comprise numbers. The radio-opaque members 1 and their corresponding indicia can be embedded in the adhesive layer 41 or may be superposed thereon. The indicia may be formed out of a radio-opaque material such as that used to form the radio-opaque members 1, or they may be made out of any other suitable material which will result in a corresponding image being formed on an X-ray film. In addition, the indicia may be separated from the corresponding radio-opaque members 1 as shown in FIG. 8A, or they may also be formed integrally with the corresponding radio-opaque members 1 as respective single pieces.

In use, the adhesive tape 40 is placed on the skin of the patient in a vicinity of the anatomic structure in question such that the radio-opaque members 1 are aligned in substantially a same plane as the anatomic structure between the X-ray tube and the film, and substantially perpendicular to the X-ray beam emitted by the X-ray tube. The size of the anatomic structure in question is then determined in the same manner as set forth hereinabove with respect to each of the other embodiments. Namely, an X-ray image is produced which includes gaps corresponding to the radio-lucent visualization gaps of any one of the radio-opaque members 1 to thereby confirm proper alignment substantially perpendicular to the X-ray beam. An apparent length of the properly aligned radio-opaque member 1 and an apparent length of the anatomic structure on the X-ray image are measured, and the size of the anatomic structure is then calculated based on the known length of the radio-opaque member 1 and the measured apparent lengths of the radio-opaque member and the anatomic structure. That is, any one of the radio-opaque members 1 which produces a gap on the X-ray image corresponding to the radio-lucent visualization gaps provided in that radio-opaque member 1 may be used to accurately determine the size of the anatomic structure in question. Thus, the disadvantage of the prior art tape scales such as that disclosed in U.S. Pat. No. 5,216,700 which may result in foreshortening of the actual size of the anatomic structure in question is thereby obviated.

In addition, the indicia of the adhesive tape 40 of the present invention can be used to enable a doctor such as an interventional radiologist to precisely locate the position of the anatomic structure in question with respect to the outside of the patient's body so that a stent, for example, may be inserted at an appropriate position within the anatomic structure. That is, when placing a stent in an artery, for example, it is not only important to know the size of the vessel but also where in the vessel a lesion is located. The adhesive tape 40 of the present invention enables both of these pieces of information to be accurately obtained. Specifically, the radio-opaque members 1 enable an accurate determination of the size of the anatomic structure, and the corresponding indicia enable an accurate determination of the location of the anatomic structure.

Figure 8B:
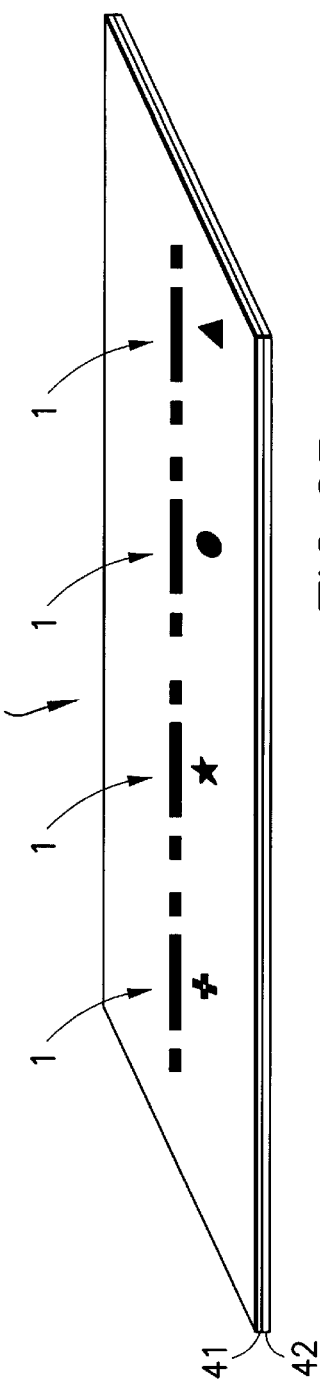
FIG. 8B is a perspective front view of alternative form of the adhesive tape embodiment shown in FIG. 8A.

FIG. 8B shows an adhesive tape 45 identical to the adhesive tape 40 shown in FIG. 8A, except that the indicia shown in FIG. 8B comprise geometric patterns.

Figure 8C:
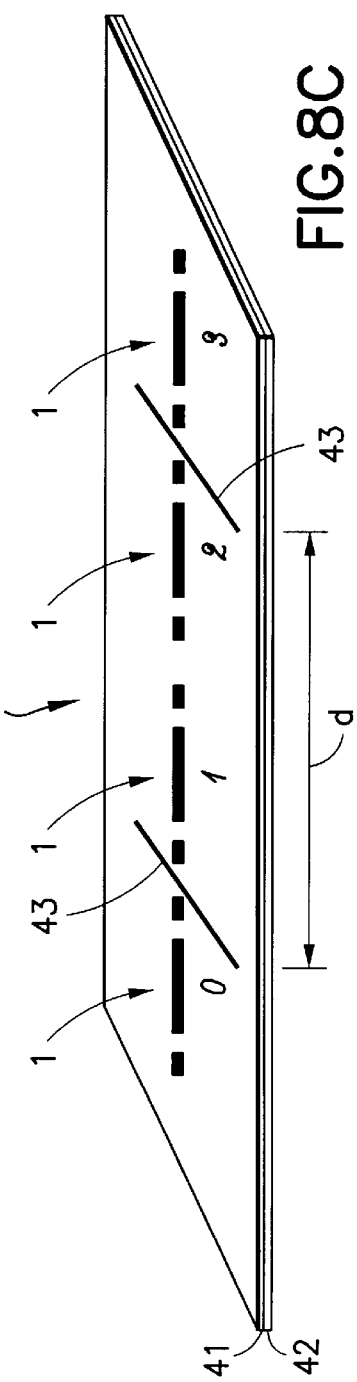
FIG. 8C is a perspective front view of alternative form of the adhesive tape embodiment shown in FIG. 8A including radio-opaque cross marks.

FIG. 8C shows an adhesive tape 50 identical to the adhesive tape 40 shown in FIG. 8A, except that radio-opaque cross marks 43 are provided for assisting a doctor or interventional radiologist is more precisely localizing a lesion and/or for enabling a very quick estimate of the size of a lesion. As shown in FIG. 8C, the radio-opaque cross marks 43 may be spaced apart from each other by a distance d. The distance d may be 5 cm, for example.

Additional advantages and modifications will readily occur to those skilled in the art. Therefore, the present invention in its broader aspects is not limited to the specific details, representative devices, and illustrated examples shown in the drawings and described herein, and various modifications may be made without departing from the spirit or scope of the present invention as defined in the appended claims.

I claim:

1. A radiological scaling device for use in determining a size of an anatomic structure on an X-ray image, said radiological scaling device comprising:
   a radio-opaque member having a predetermined known dimension associated therewith, and first and second radio-lucent visualization gaps positioned symmetrically at respective end portions of the radio-opaque member;
   wherein the predetermined known dimension is a total length of the radio-opaque member between outer end points thereof; and
   wherein the total length of the radio-opaque member is approximately 2.0 cm, and the first and second radio-lucent visualization gaps are equal in size and are each approximately 0.3–0.5 mm in length.

2. The radiological scaling device of claim 1, further comprising a radio-lucent housing in which the radio-opaque member is provided.

3. The radiological scaling device of claim 2, further comprising a handle portion coupled to the housing.

4. The radiological scaling device of claim 3, wherein the handle portion is arranged perpendicular to the housing such that the radiological scaling device has a T-shaped configuration.

5. The radiological scaling device of claim 2, further comprising a layer of adhesive provided on an external surface of the housing for attaching the radiological scaling device to an external surface of a patient, and a removable cover strip provided on the adhesive.

6. The radiological scaling device of claim 1, further comprising a catheter in which the radio-opaque member is provided.

7. The radiological scaling device of claim 6, wherein the radio-opaque member is longitudinally arranged along a length of the catheter.

8. The radiological scaling device of claim 6, wherein the catheter is made of a substantially radio-lucent material.

9. A radiological scaling device for use in determining a size of an anatomic structure on an X-ray image, said radiological scaling device comprising:

two radio-opaque members separated by a predetermined known distance, and each having a radio-lucent visualization gap provided therein;

wherein the predetermined known distance is a total length between one of inner and outer end points of the radio-opaque members; and wherein the total length is approximately 2.0 cm, and the radio-lucent visualization gaps are equal in size and are each approximately 0.3–0.5 mm in length.

10. The radiological scaling device according to claim 9, wherein at least one of said two radio-opaque members comprises a radio-opaque washer having a radio-lucent visualization gap provided in a center portion thereof.

11. The radiological scaling device according to claim 9, wherein each of said two radio-opaque members comprises a radio-opaque washer having a radio-lucent visualization gap provided in a center portion thereof.

12. An adhesive tape for use in determining a size of an anatomic structure on an X-ray image, comprising:

a plurality of longitudinally arranged radio-opaque members each having a predetermined known dimension associated therewith and each having first and second radio-lucent visualization gaps positioned symmetrically at respective end portions thereof; and a plurality of indicia each corresponding to a respective one of said radio-opaque members;

wherein the predetermined known dimension associated with each of the radio-opaque members is a total length between outer end points of each of the radio-opaque members; and wherein the total length of each of the radio-opaque members is approximately 2.0 cm, and the first and second radio-lucent visualization gaps are equal in size and are each approximately 0.3–0.5 mm in length.

13. The adhesive tape according to claim 12, wherein the adhesive tape is made of a substantially radio-lucent material, and the plurality of indicia are made of a radio-opaque material.

14. The adhesive tape according to claim 12, further comprising a plurality of radio-opaque cross marks provided between respective ones of said radio-opaque members at a predetermined interval.

15. A method for determining a size of an anatomic structure comprising:

arranging a radio-opaque member in a vicinity of the anatomic structure such that the radio-opaque member is aligned to be: (i) in substantially a same plane as the anatomic structure between an X-ray tube and a film, and (ii) substantially perpendicular to an X-ray beam emitted by the X-ray tube, said radio-opaque member having a predetermined known dimension associated therewith and including at least one visualization gap;

producing an X-ray image including at least one gap corresponding to the at least one visualization gap of the radio-opaque member to thereby confirm that the radio-opaque member has been properly aligned substantially perpendicular to the X-ray beam;

determining an apparent length of the known dimension and an apparent length of the anatomic structure on the X-ray image;

calculating the size of the anatomic structure based on the known dimension, and the measured apparent lengths of the known dimension and the anatomic structure.

16. The method according to claim 16, wherein the radio-opaque member is provided in a radio-lucent housing, and the arranging step comprises manipulating a position of the housing to arrange the radio-opaque member at a position on an external surface of a patient in the vicinity of the anatomic structure such that the radio-opaque member is aligned to be: (i) in substantially the same plane as the anatomic structure between the X-ray tube and the film, and (ii) substantially perpendicular to the X-ray beam emitted by the X-ray tube.

17. The method according to claim 15, wherein the radio-opaque member is provided in a catheter, and the arranging step comprises inserting the catheter into a patient in the vicinity of the anatomic structure such that the radio-opaque member is aligned to be: (i) in substantially the same plane as the anatomic structure between the X-ray tube and the film, and (ii) substantially perpendicular to the X-ray beam emitted by the X-ray tube.

* * * * *